United States Patent [19]
Shaw

[11] Patent Number: 5,779,679
[45] Date of Patent: Jul. 14, 1998

[54] WINGED IV SET WITH RETRACTABLE NEEDLE

[76] Inventor: Thomas J. Shaw, 1510 Hillcrest, Little Elm, Tex. 75068

[21] Appl. No.: 845,762

[22] Filed: Apr. 18, 1997

[51] Int. Cl.⁶ .................................................. A61M 5/178
[52] U.S. Cl. .......................... 604/158; 604/164; 604/177
[58] Field of Search .................................. 604/158, 164, 604/165, 171, 263, 172, 198, 177

[56] References Cited

U.S. PATENT DOCUMENTS

| | | | |
|---|---|---|---|
| 4,820,282 | 4/1989 | Hogan | 604/263 |
| 5,088,982 | 2/1992 | Ryan | 604/110 |
| 5,120,320 | 6/1992 | Fayngold | 604/177 |
| 5,192,275 | 3/1993 | Burns | 604/263 |
| 5,267,961 | 12/1993 | Shaw | 604/110 |
| 5,330,438 | 7/1994 | Gollobin et al. | 604/177 |
| 5,376,075 | 12/1994 | Haughton et al. | 604/158 |
| 5,385,551 | 1/1995 | Shaw | 604/110 |
| 5,389,076 | 2/1995 | Shaw | 604/110 |
| 5,407,431 | 4/1995 | Botich et al. | 604/110 |
| 5,407,436 | 4/1995 | Toft et al. | 604/195 |
| 5,409,461 | 4/1995 | Steinman | 604/110 |
| 5,423,758 | 6/1995 | Shaw | 604/110 |
| 5,562,634 | 10/1996 | Flumene et al. | 604/171 |
| 5,573,510 | 11/1996 | Isaacson | 604/158 |
| 5,578,011 | 11/1996 | Shaw | 604/110 |
| 5,676,658 | 10/1997 | Erskine | 604/164 X |

*Primary Examiner*—John D. Yasko
*Attorney, Agent, or Firm*—Locke Purnell; Rain Harrell

[57] ABSTRACT

The present invention addresses a winged IV set having a retractable needle which provides additional safety to health care workers from accidental needle sticks. The winged IV set would consist of a device body with two sets of wings, one for handling and one for retraction, a needle, a needle holder with a nipple extension which may be connected with the catheter or IV tube, and a spring. The needle holder has opposed U-shaped arms which terminate in lugs that are received in opposed openings in the device body. The pair of retraction wings have a corresponding pair of tabs such that when the wings are folded, the tabs push the lugs out of the openings, allowing the spring to drive the needle and the needle holder back into the device body where another set of openings in the body receive the lugs on the needle holder to retain the needle inside the body. After retraction the device body may be handled safely.

17 Claims, 5 Drawing Sheets

WINGED IV SET WITH RETRACTABLE NEEDLE

FIELD OF THE INVENTION

The invention is a medical device designed to insert and maintain in place an IV and to allow for retraction of the needle in the removal process to significantly decrease the possibility of inadvertent needle sticks into the patient or health care workers.

BACKGROUND OF THE PRIOR ART

Winged IV sets are well known in the art. When a patient is to receive intravenous delivery of a fluid, use of a needle connected through a winged body to an IV tube is not uncommon. The wings are used to handle the assembly during insertion and withdrawal. The wings are also used to stabilize the device while in place by providing a broad surface area of contact with the patient which allows for taping of the device to the patient while discouraging movement, especially rotation, of the device. Upon withdrawal, however, the needle which is now contaminated with blood or other body fluid must be disposed of without creating a risk of needle sticks to medical personnel which are engaged in the operation of withdrawing the winged IV set. A danger to clean up and medical waste disposal personnel continues if the used needles are not rendered harmless in some way. Caps or covers that can be mounted over the needle are not a satisfactory solution because they must be put in place and can come loose and expose the used needle.

While there is substantial prior art on winged IV sets intended to reduce the possibility of needle sticks, viewed as a whole, this art teaches a different approach than that taken in the current invention.

U.S. Pat. No. 5,088,932 to Ryan for Safety Winged Needle Medical Devices discloses a double wing IV set in which a slidable hollow winged shield is used to cover a removed needle. One set of wings is attached to a hollow winged shield and one set of wings to a hollow inner tube encircled in part by the hollow winged shield. During use, the shield is frictionally engaged over one end of the inner tube which carries the needle on its other end. When finished, the needle is covered by separately gripping the sets of wings to move the shield forward relative to the inner tube until the shield is locked into position covering the needle.

U.S. Pat. No. 5,120,320 to Fayngold for IV Infusion or Blood Collection Assembly w/Automatic Safety Feature discloses a single wing IV set which uses a separate slidable two-part shield to cover a removed needle/tube assembly. The shield may be opened and positioned around the needle/tube assembly rather than requiring a threading process. Once in place, the needle is covered by pulling the assembly back through the shield which uses guide grooves for the wings to control orientation and to deliver the wings over a ledge into a rear slot which locks the system in its covered position.

U.S. Pat. No. 5,330,438 to Gollobin et al. for Protective Sheath for Butterfly Needles and IV Infusion Set and Sheath Assembly and U.S. Pat. No. 5,192,275 to Burns for IV Infusion or Blood Collection Guard Assembly both disclose single wing IV sets which use slidable protective sheaths to cover removed needle/tube assemblies. The sheaths are manually slid over the assembly to cover the needle. Gollobin locks the sheath in the covered position by capturing the wings in a fashion similar to Fayngold (above), while Burns' cover has grooves to allow the wings to travel past but does not appear to positively interact with the wings. The cover in Burns is locked in the extended position by locking lugs on the housing which drop off a ledge into indentations or slots.

U.S. Pat. No. 5,409,461 to Steinman for Catheter Introducer Assembly with Needle Shielding Device discloses a winged catheter introducer in which a needle is used to introduce an IV tube into the patient, and then drawn back manually through the tube and into a holding container for safe storage, leaving a catheter in place to provide fluid communication between the patient and the IV. The wings are not involved in the retraction of the needle.

U.S. Pat. No. 5,407,436 to Toft et al. for Syringe with Retractable Needle discloses a standard syringe with a spring-loaded retractable needle. A needle-holder is held in place against a compressed spring by latch fingers having shoulders facing radially inward and having actuating surfaces. On the end of the plunger is a plug which is held in place by latching fingers (with shoulders facing radially outwards) which have surfaces which interact with the actuating surfaces of the needle holder. When plunger motion is continued forward after initial contact between the respective actuating surfaces, the slopes of these surfaces result in fingers being pushed radially outward and inward respectively until the shoulders of each slip off and the spring is able to drive the needle-holder, needle, and plug back into the hollow body of the plunger.

U.S. Pat. No. 5,407,431 to Botich et al. for Intravenous Catheter Insertion Device with Retractable Needle discloses a standard syringe with a spring-loaded retractable needle. A needle-holder is held in place against a compressed spring by resilient fingers with hooks or shoulders. The plunger has a frangible end which when subjected to a normal force of 2 pounds will dissociate from the plunger. When the frangible end is pressed against the resilient fingers the fingers are spread radially outward until the hooks no longer restrain the needle-holder. The force of the compressed spring passing through the needle-holder breaks free the frangible end resulting in the needle-holder with needle and the frangible end being pushed back into the hollow body of the plunger. Botich also discloses a catheter insertion device. Both of the Botich devices similarly employ retaining fingers to restrain the needle-holder until a plunger pushes them radially outward releasing the spring.

While the prior art does recognize the advantages of protection against needle sticks, almost all of the safety winged IV sets rely on manual sliding of a cover over the needle. Only one set was found which relied on retraction of the needle with respect to the overall device, and it does so by manually drawing back the needle through the tube using what is effectively a string attached to the rear of the needle. The needle moves into a holding container for safe storage, leaving a catheter in place to provide fluid communication between the patient and the IV. No winged IV sets employ a spring loaded retraction system. There are, of course, disclosures of retractable needle systems used in syringes, but no suggestion is made to combine these concepts. Given the significant differences in use between winged IV sets, which are typically taped to the patient and left in place for extended periods of time, and syringes, which are inserted within the patient only briefly, it is easy to see how the type of retraction systems used in syringes and the like have apparently never been applied with winged IV sets for fear of accidental retraction during the extended time the IV is maintained in the patient.

Even the safety systems which are present in prior art winged IV sets are problematic. They almost always involve the need for two handed operation and may not be used until after the needle is removed and clear of the patient. Additionally some of the systems must be threaded onto preexisting winged IV sets creating additional difficulty for health care workers prior to insertion. They also open the possibility for additional error if improperly put in place. Finally almost all of the systems require the health care workers to put their hands around and near the exposed needle in order to slide the cover or sheath into place around it. These problems are reduced or eliminated by the present invention.

SUMMARY OF THE INVENTION

The present invention is a winged IV set having a retractable needle. The preferred embodiment of the set would be initially supplied with the needle extended. The exposed needle would have a removable cover or cap over it.

In the preferred winged IV set of the current invention, the needle is mounted in a needle holder having a passage in fluid communication with a nipple on the opposite end to which a catheter tube (or IV tube) leading to a fluid bottle would be attached. The needle holder has opposed U-shaped arms which terminate in lugs that are received in opposed openings in the body of the device. The needle holder is pre-loaded with a spring for movement in a retraction direction when the lugs are released from the openings in the device body.

In the preferred winged IV set of the current invention, the body has a large pair of "wings" which are used for handling the device (which are specifically referred to herein as handling wings). A smaller pair of "retraction wings" are molded as part of the body. The folding retraction wings each have a tab which pushes one of the lugs out of the openings when the retraction wings are folded by the health care worker. A fold line is molded into each retraction wing to facilitate folding. There are no rotating parts. In the preferred embodiment, the device body is flat on one side, which provides a stable base when placed against the patient.

The winged IV set of the preferred embodiment of this invention is used as a normal winged IV set for insertion and maintenance during the time the set is providing IV fluid to the patient. However, when the needle is removed from the patient the retraction wings may be folded using one hand, releasing the lugs from the openings in the device body, and allowing the spring to drive the needle and the needle holder back into the body where another set of openings receive the lugs on the needle holder to safely lock or retain the needle within the device body. After retraction, the body can be safely handled.

One skilled in the art will recognize that the concepts of this invention will likewise apply to other medical devices for inserting and maintaining in place an IV, even if those devices do not have the pair of handling wings of a typical winged IV set.

DETAILED DESCRIPTION OF THE PREFERRED EMBODIMENT

Figure 1:
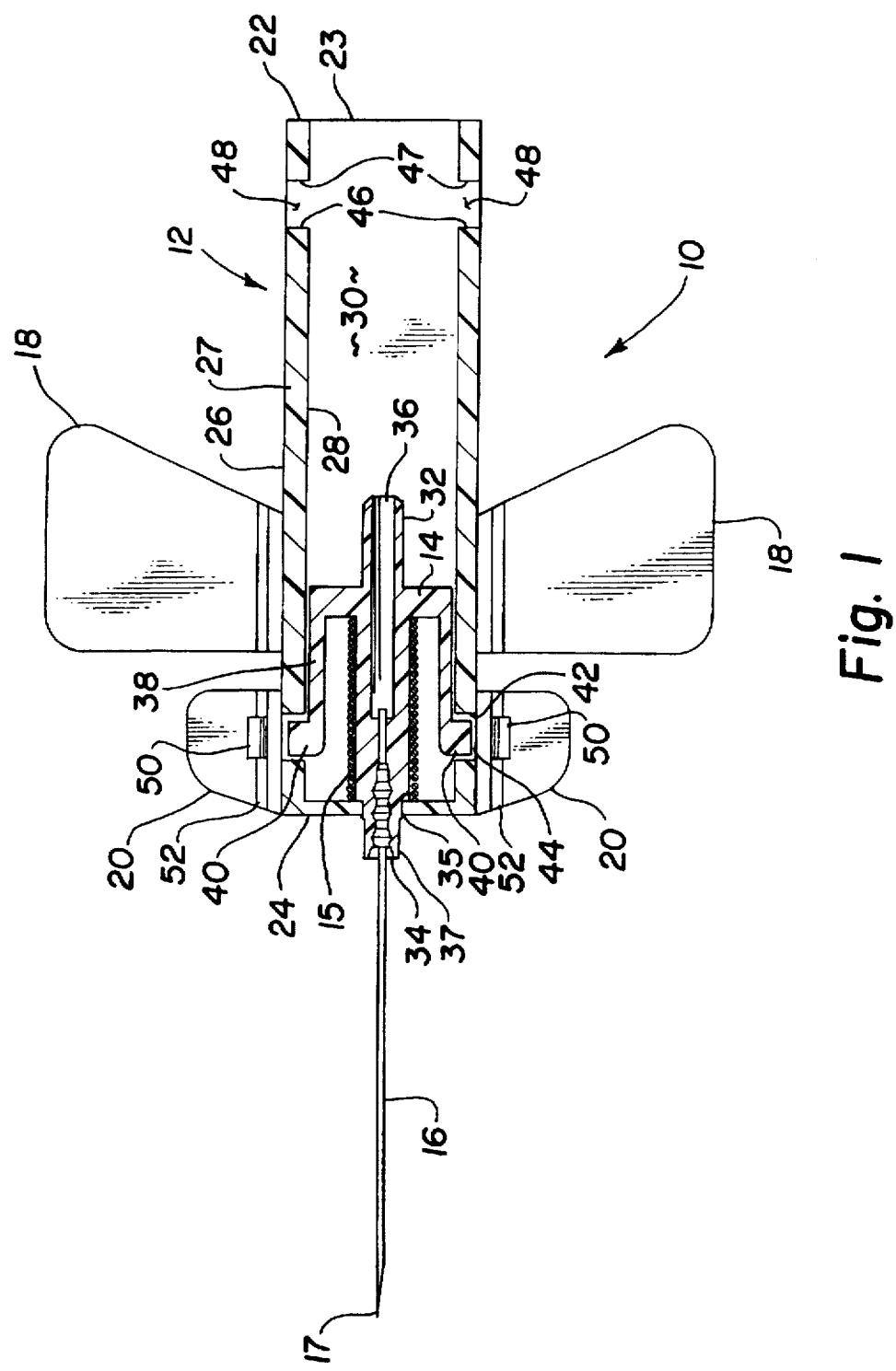
FIG. 1 is a cut-away view of the preferred embodiment in its extended position, viewed from above, with the spring compressed and the lugs received within openings near the front end of the device body.

FIG. 1 shows winged IV set 10 of the current invention in its extended position. Three major components illustrated in this Figure are: device body 12, needle holder 14, and spring 15. Needle 16, which extends from needle holder 14, has a sharpened tip 17. Needle 16 may be any hollow tubular member which may be inserted and maintained within the patient and which maintains fluid communication between the patient and an IV tube through the IV set.

Device body 12 (which may also be referred to herein as body 12) has an elongated hollow body. Device body 12 preferably has a pair of handling wings 18 and a pair of retraction wings 20. Back end 22 of body 12 (which may also be referred to herein as back end portion 22 or nipple end 22) contains an opening 23. Front end 24 (which may also be referred to herein as front end portion 24 or needle end 24) contains an opening 25 (better illustrated in FIG. 2). The middle portion of device body 12 includes a longitudinally extended wall 27 extending from the front end portion 24 to the back end portion 22. Wall 27 has an outer surface 26 (which may also be referred to herein as the outer surface of the middle portion) and an inner surface 28 (which may also be referred to herein as the inner surface of the middle portion). Hollow portion 30 (which may also be referred to herein as cavity 30) is defined and bounded by wall 27, front end portion 24, and back end portion 22.

Needle holder 14 in FIG. 1 has a nipple 32 which extends toward back end 22 of body 12. Nipple 32 is configured to allow the connection of a catheter or IV tube in various manners as would be familiar to one skilled in the art. Needle holder 14 also has a front end 34 (which may also be referred to as needle end 34). This front end 34 circumferentially engages needle 16 and holds it firmly in place. Needle holder 14 further has a pair of U-shaped opposing arms 38 [note that throughout this application, opposing may be interpreted to be an approximation of relative position and not a strictly constructed requirement] extending out and towards front end 24 of body 12. In the illustrated embodiment, these arms 38 are attached to needle holder 14 near nipple 32 of needle holder 14. Arms 38 could extend from further up needle holder 14, so long as arms 38 are of sufficient length to allow the flexing needed to operate the retraction mechanism, and so long as needle 16 and device body 12 are appropriately dimensioned to provide proper positioning in both the extended and retracted position. In the extended position, a significant portion of needle 16 extends past front end 24 of body 12 so that it can be inserted into the patient. In the retracted position, needle 14 is completely contained within hollow portion 30 of body 12.

Needle holder 14's opposing arms 38 each terminate in a lug 40. Lugs 40 are used to position and maintain (or lock) needle holder 14 in each of its two positions (extended and retracted) of the preferred embodiment. In an alternative embodiment, lugs 40 may only act to lock needle holder 14 in the extended position, with the position after retraction being more loosely defined and maintained. In its extended position of FIG. 1, lugs 40 of needle holder 14 would be driven into contact with a pair of opposing shoulders 42 in device body 12 by spring 15 which biases needle holder 14 towards back end 22 of body 12. Opposing shoulders 42 are formed by a pair of opposing openings 44 in wall 27 of body 12 located near needle end 24, and provide a countering reaction force to the biasing force generated by spring 15. Shoulders 42 effectively retain needle holder 14 in the extended position where needle end 34 of needle holder 14 extends through opening 25 of front end 24 of body 12. With lugs 40 positioned in openings 44 against shoulders 42, needle holder 14 is locked in its extended position. This position may also be referred to herein as its forward locked position.

Needle end 34 of needle holder 14 has a reduced diameter nose 37 which extends from the larger diameter center section 39 of needle holder 14 at shoulders 35. In the extended position, nose 37 protrudes through opening 25 in front end 24 of body 12, but shoulders 35 (as well as tubular center section 39 of needle holder 14 (see FIG. 4) behind and defining shoulders 35) are of a larger diameter than opening 25 and therefore define the furthest needle holder 14 may extend past front end 24 of body 12. The position of the lugs 40 within openings 44 will also define how far forward needle holder 14 may be positioned, so shoulders 35 are not strictly necessary. Another pair of openings 48 in the middle portion of device body 12 located near nipple end 22 result in two opposing pairs of shoulders, a pair of retaining shoulders 47 and a pair of safety shoulders 46, whose role and function will become more apparent when examining FIG. 2 shortly.

The pair of retraction wings 20 have two key features which assist in the retraction efforts. Each retraction wing 20 has a tab 50 which is aligned with an opening 44 in device body 12. In the illustrated embodiment, retraction wings 20 each have a premolded fold line 52. Although not required, fold lines 52 increase the ability to predictably and easily fold retraction wings 20 in order to maintain proper alignment of tabs 50 to accomplish retraction. Retraction wings 20 are shown in the preferred embodiment as a pair of smaller wings paralleling handling wings 18. This basic alignment of two pairs of wings possesses a surface resemblance to the double-winged IV sets familiar to those skilled in the art. For the purposes of this invention, however, retraction wings 20 could consist of any extension (including a bendably attached or bendable lateral extension) or attachment coupled to tabs 50 enabling the user to push tabs 50 into openings 44 to release lugs 40. Such alternate structures could be visualized by those skilled in the art.

Figure 2:
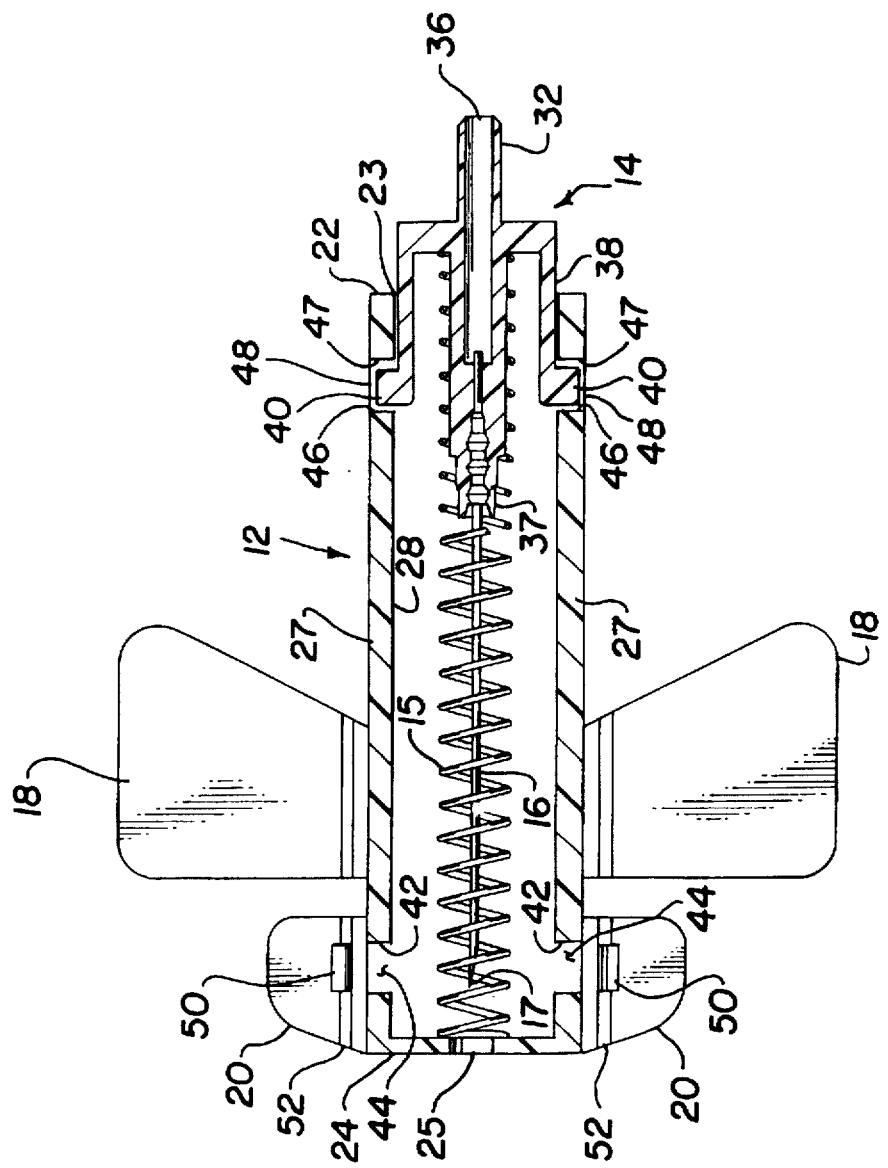
FIG. 2 is the cut-away view of the preferred embodiment of FIG. 1 in its retracted position, with the spring extended, the lugs received within the openings near the back end of the device body, and the needle fully contained within the body.

When the preferred retraction wings 20 are folded towards each other along fold lines 52, tabs 50 move into openings 44, contact lugs 40 and start pushing lugs 40 into hollow portion 30 of body 12. Lugs 40 are able to move towards hollow portion 30 of body 12 because opposing arms 38 are flexible enough and long enough to flex inward in response to the pressure on the ends (lugs 40) provided by tabs 50. When lugs 40 have been pushed inward far enough to leave shoulders 42, there is no longer a restraining force opposing the bias placed on needle holder 14 by spring 15 and the arms 38 and lugs 40 are now in an unlocked position. Needle holder 14 will then start sliding back within hollow portion 30 of body 12 in response to force from spring 15 as it extends. As needle holder 14 is sliding backwards towards back end 22 of body 12, lugs 40 will slide along inner surface 28 of body 12 as opposing arms 38 attempt to spring back from an unlocked position to their relaxed position. As needle holder 14 moves towards back end 22 of body 12, lugs 40 will slip into openings 48 and be contained between opposing pairs of shoulders 46 and 47. With lugs 40 contained between opposing pairs of shoulders 46 and 47, needle holder 14 is locked in the retracted position. This is its rearward locked position as illustrated in FIG. 2. For lugs 40 to successfully slip into openings 48, opposing arms 38 are "springing arms" resilient enough to spring back towards their original position when opposing forces and structures are not interfering.

FIG. 2 shows needle holder 14 in the retracted position. Needle 16 is entirely contained within device body 12. Spring 15 is in a less compressed state. Spring 15 must be positioned and sized such that sufficient biasing force to slide needle holder 14 will continue at least until lugs 40 move completely behind shoulders 46. In the rearward locked position, needle holder 14 is prevented from moving toward the needle end 24 of body 12 by the interaction between lugs 40 and safety shoulders 46 created by openings 48. In this retracted position, needle holder 14 is prevented from going completely out of the back end 22 of body 12 by the pair of opposing retaining shoulders 47 and their interaction with lugs 40. Thus needle holder 14 and needle 16 are safely secured in their retracted position. Alternative embodiments may rely on a lip or constriction in opening 23 of back end 22 to retain needle holder 14 instead of openings 48.

FIG. 2 illustrates the retracted position. In the retracted position, reduced diameter nose 37 of needle holder 14 does not fill opening 25 and openings 44 in wall 27 of body 12 are not filled by lugs 40. Finally nipple 32 extends out back end 22 of body 12 through opening 23. One skilled in the art will recognize that nothing has occurred through the process of getting to this retracted position which would have removed or caused a need to remove an attached catheter or IV tube. Once needle 16 is safely within device body 12, the catheter or IV tube attached to nipple 32 may be safely and easily removed at any time at the convenience of the health care technician.

Figure 3:
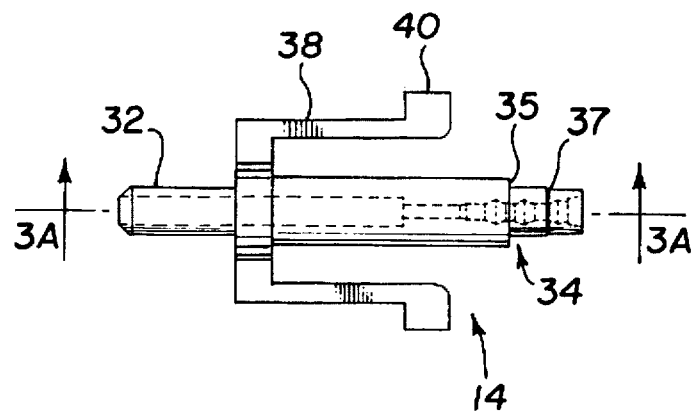
FIG. 3 shows the needle holder of the preferred embodiment, without the needle, spring or device body, again viewed from above.
Figure 3A:
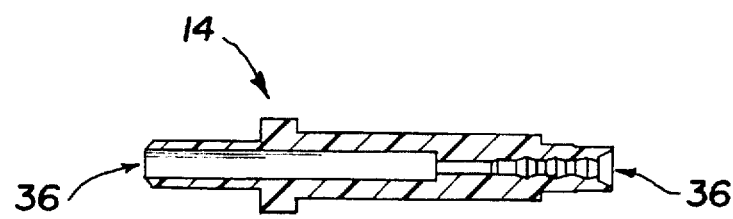
FIG. 3A shows a cut-away view of the needle holder of FIG. 3 along the line A—A.
Figure 3B:
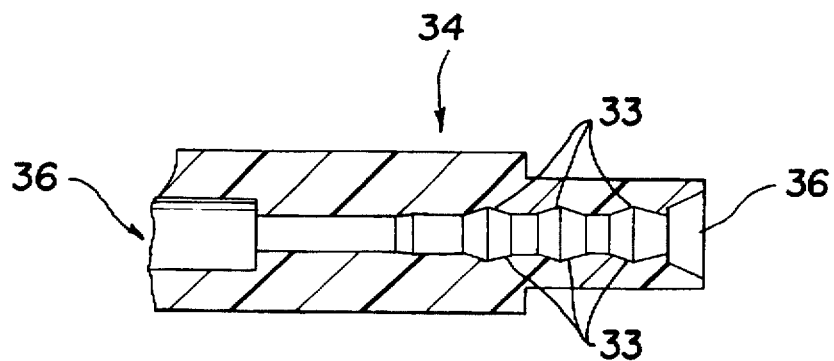
FIG. 3B is a detail drawing focusing on the needle end of the needle holder of FIG. 3A.

FIG. 3 provides an isolated view of needle holder 14. FIG. 3 includes nipple 32, needle end 34, and opposing arms 38 terminating in lugs 40. In the cut away view, FIG. 3A, needle holder 14 is recognizably hollow, having a passage 36 which travels completely through needle holder 14. This hollow passage 36 enables needle holder 14 to create a fluid communication between needle 16 (which is also hollow) and a catheter or IV tube attached around nipple 32. In FIG. 3B, needle end 34 of needle holder 14 has structures 33 which are used to hold glue to attach needle 16. Structures 33 comprise one method of several familiar to those skilled in the art which enable needle holder 14 to seal and hold needle 16 in position for use.

Figure 4:
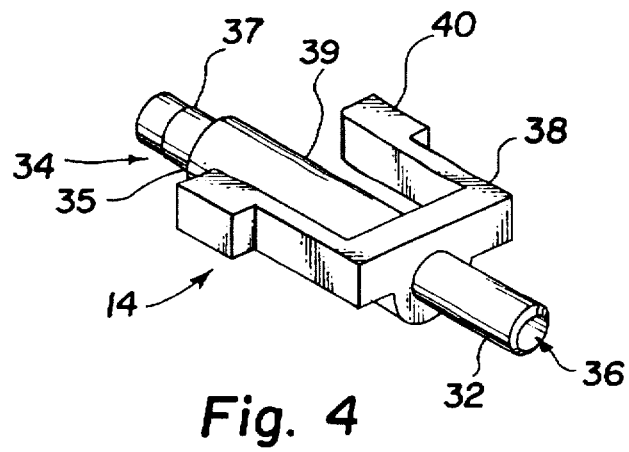
FIG. 4 illustrates a three dimensional view of the needle holder viewed from a rear side angle.

FIG. 4 provides a three dimensional line view of needle holder 14 including passage 36, opposing arms 38 and lugs 40, nipple 32, tubular center section 39, and reduced diameter nose 37 and shoulders 35 in the needle end 34 of needle holder 14.

Figure 5:
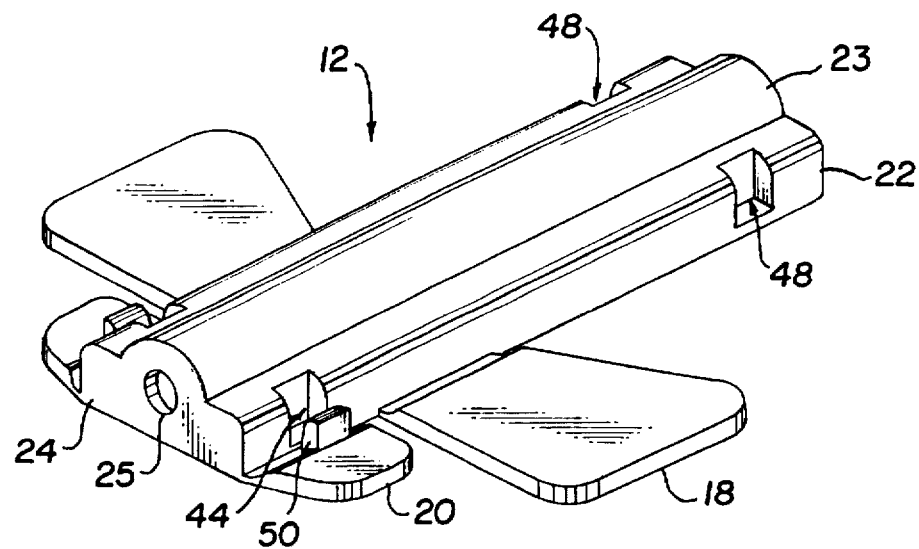
FIG. 5 is a perspective outline of the device body of the preferred embodiment, without the needle, needle holder, or spring, viewed from a front side angle.

FIG. 5 provides a three dimensional line view of the isolated device body 12 without needle holder 14, needle 16, or spring 15 present. This three dimensional view gives an additional perspective on openings 48 towards nipple end 22 of body 12 and on openings 44 towards needle end 24 of body 12 and their relationship to tabs 50 and retraction wings 20. FIG. 5 shows a preferred shape of opening 25 in front end 24 of body 12 and opening 23 in back end 22 of body 12. Openings 44 and 48 extend laterally but not vertically all the way through device body 12. Alternative approaches to this positioning of openings 44 and 48 may be called for depending on the manufacturing process, materials, and overall shape of device body 12.

Figure 6:
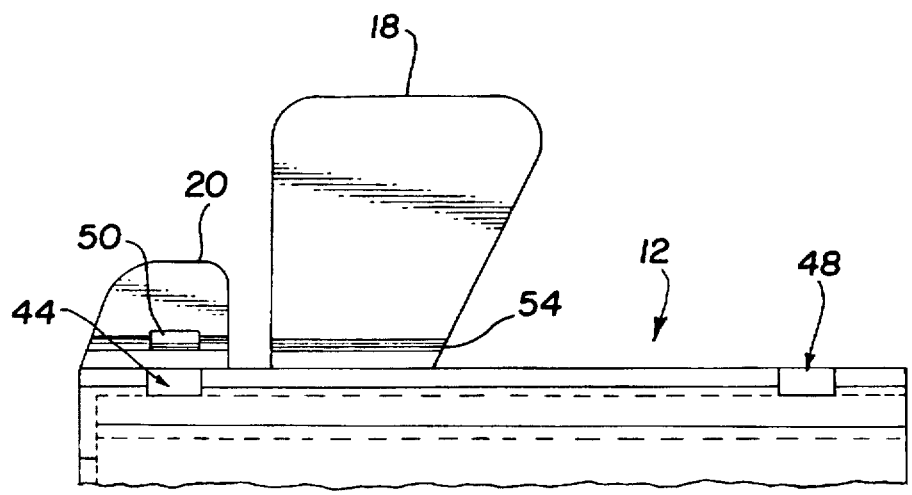
FIG. 6 presents one half of the isolated device body viewed from above.

FIG. 6 provides a further top view of one-half of device body 12. Handling wing 18 may have a fold line 54. Although illustrated in this embodiment, this is not necessary to the function of the winged IV set as a whole. The additional fold lines 54 do, however, provide a little more flexibility in handling wings 18 for use in attaching the winged IV set to the patient as will be discussed momentarily. In the illustrated embodiment, handling wings 18 are shown as being roughly trapezoidal in shape with rounded corners. However, the present invention does not in any way rely on the shape and size of the handling wings, such that any of numerous shapes and sizes of wings from winged IV sets known and used by those skilled in the art would be appropriate.

Figure 7:
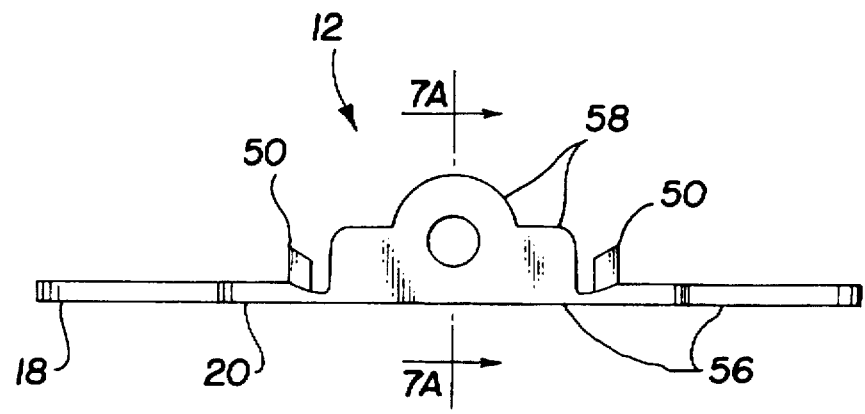
FIG. 7 presents a front view of the silhouette of the device body showing tabs which engage the lugs and the shape of the device body.
Figure 7A:
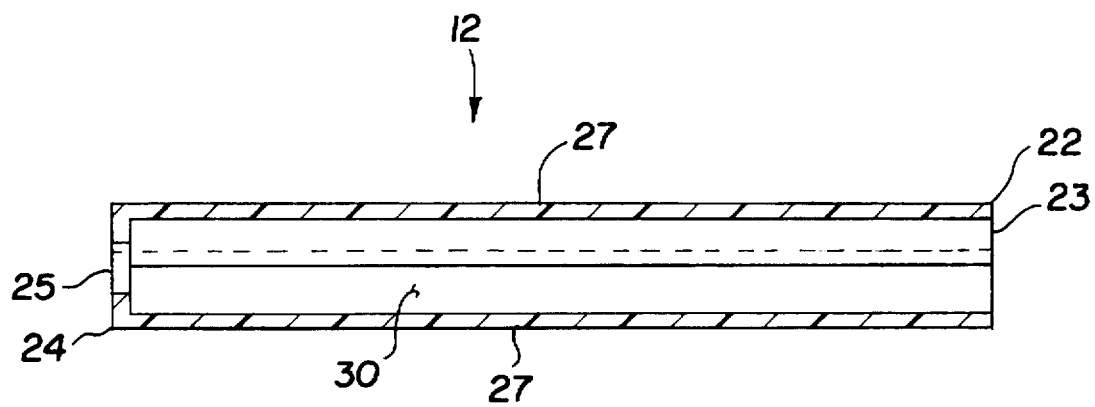
FIG. 7A shows a cut away view of the device body of FIG. 7 along the line A—A.

Finally, FIG. 7 provides a silhouette front view of the isolated device body 12. The lower surface (or bottom surface) of device body 12 and of wings 18 & 20 define a planar surface 56 (which represents the congruence of the plane defined by each of those elements). This flattened surface 56 is preferable, although not necessary, again to provide ease of attachment of the winged IV set to the patient. In alternative embodiments the planes defined by wings 18 & 20: may be only parallel to the bottom surface of device body 12 (while still being congruent or approximately congruent with each other); may only be parallel to each other; may not be parallel to each other or the bottom surface; or either or both of the pairs of wings 18 and 20 may not even define a plane. FIG. 7 shows a silhouette end view of tabs 50 on retraction wings 20. Device body 12 is basically a rectangle, with the bottom surface aligning with the bottom surface of the wings 18 & 20 as discussed. The upper surface 58 of body 12 includes a semi-circular cross section which accommodates and conforms around the tubular center section 39 of needle holder 14 (for a view of the shape of center section 39 see FIG. 4). Alternatively, device body 12 could be a larger rectangle and still accommodate needle holder 14 or any of various other shapes and still accomplish the main goals of the present invention. FIG. 7A illustrates a cut away side view of FIG. 7. FIG. 7A shows opening 25 in front end 24, opening 23 in back end 22, wall 27, and cavity 30 bounded by wall 27, front end 24, and back end 22.

In practice, winged IV set 10 is provided in its extended position as shown in FIG. 1. The extended needle 16 and tip 17 are covered by a separate cap or cover (not illustrated) in any of several manners familiar to one skilled in the art. Prior to insertion into the patient, a catheter or IV tube is threaded or attached to nipple 32 in sealable contact and fluid communication. The cap is then removed, exposing needle 16 and point 17, and using device body 12 and handling wings 18 the winged IV set is guided such that needle 16 is inserted into an appropriate blood vessel of the patient. Winged IV set 10 is then placed with surface 56 down against the skin of the patient and secured into place using tape. In this way, winged IV set 10 is securely and stably attached to the patient until such time as it needs to be removed or replaced.

An important aspect of the operation is the fact that the operator can conveniently release and thereby retract needle 16 to a covered position with one hand. This may be accomplished as the actual act of removing the needle from the patient, or anytime starting immediately after the needle is removed from the patient (recognizing that it is preferable to retract needle 16 as soon as possible thereby reducing the time of exposure to accidental needle sticks). One handed operation is possible in that two fingers (e.g., the forefinger and the thumb) may be used to fold retraction wings 20 towards each other. The folding of retraction wings 20 pushes lugs 40 off of shoulders 42 thus allowing spring 15 to retract needle 16 to a covered position (or retracted position). The other hand is free to grasp the catheter or IV tube, the patient, the handling wings 18, or the device body 12 as necessary. Timing for releasing the retractable needle 16 and later separating the catheter or IV tube from nipple 32 of needle holder 14 is under complete control of the medical technician.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

I claim:

1. A medical device for temporarily establishing venous fluid communication between a patient and a source of fluid comprising:

an elongated hollow body having a longitudinally extended wall defining a cavity therein, the body having a front end portion, a back end portion, and a middle portion extending between the end portions;

a sliding needle holder configured to fit within the cavity and slide backwards from a forward locked position, the needle holder having a centrally positioned tubular connection having a front portion capable of holding a needle and a rear portion capable of receiving an end of a tubular fluid connection;

the middle portion of the elongated body having at least one laterally extending opening near the front end portion of the body which is adapted to receive a lug;

the sliding needle holder having at least one springing arm terminating in a lug which in an unlocked position allows the needle holder to slide within the cavity, the sliding needle holder being positionable in the forward locked position wherever the lug on the springing arm engages the lug receiving opening near the front end portion of the elongated body to hold the sliding needle holder in position for insertion of a needle extending from the front end portion of the body; and, a bendably attached lateral extension of the body having a tab oriented to engage and release the lug from the laterally extending opening near the front end portion of the elongated body to permit the needle holder to be driven rearwardly by a spring thereby retracting the needle within the elongated body.

2. The medical device of claim 1 wherein:

the sliding needle holder slides between the forward locked position and a rearward locked position;

the middle portion of the elongated body has at least one laterally extending opening near the back end portion of the body which is adapted to receive a lug; and, the sliding needle holder is positionable in the rearward locked position wherever the lug on the springing arm engages the lug receiving opening near the back end portion of the body to hold the sliding needle holder in position wherein the needle is contained within the elongated body.

3. The medical device of claim 2 wherein:

the laterally extending opening near the front end portion of the body is a pair of laterally extending openings, each of which is adapted to receive a lug;

the laterally extending opening near the back end portion of the body is a pair of laterally extending openings, each of which is adapted to receive a lug;

the springing arm is a pair of springing arms, each terminating in a lug, which in an unlocked position allow the needle holder to slide within the cavity;

the forward locked position is wherever the lugs on the springing arms engage the lug receiving openings near the front end portion of the elongated body to hold the sliding needle holder in position for insertion of a needle extending from the front end portion of the body;

the rearward locked position is wherever the lugs on the pair of springing arms engage the lug receiving openings near the back end portion of the body to hold the sliding needle holder in position wherein the needle is contained within the elongated body;

the bendably attached lateral extension is a pair of bendably attached lateral extensions of the body, each having a tab oriented to engage and release one of the lugs from one of the laterally extending openings near the front end portion of the elongated body to permit the needle holder to be driven rearwardly by a spring thereby retracting the needle within the elongated body; and, the body has a flattened wall portion along one side and laterally extending extensions associated with the flattened wall portion for taping the body with the flattened wall portion against a patient's skin after fluid communication has been established.

4. The medical device of claim 3 wherein:

the pair of laterally extending openings near the front end portion of the body is a pair of approximately opposing laterally extending openings;

the pair of springing arms is a pair of approximately opposing springing arms;

the pair of bendably attached lateral extensions is a pair of approximately opposing bendably attached lateral extensions of the body; and, the pair of laterally extending openings near the back end portion of the body is a pair of approximately opposing laterally extending openings.

5. The medical device of claim 4 wherein:

the laterally extending extensions associated with the flattened wall portion for taping the body with the flattened wall portion against a patient's skin after fluid communication has been established are an approximately opposing pair of laterally extending extensions.

6. A winged IV set comprising:

a device body having a front end, a back end, a middle portion comprising a longitudinally extended wall, and a hollow portion between the front and back ends and bounded by the wall of the middle portion;

a pair of approximately opposing handling wings extending from the longitudinally extended wall of the middle portion of the device body;

a needle holder within the hollow portion of the device body;

at least one arm extending from the needle holder;

the arm terminating in a lug;

a needle extending outwardly from the needle holder in the direction of the front end of the device body;

a resilient member in contact with the device body and the needle holder and positioned to create a biasing force on the needle holder away from the front end of the device body;

a shoulder in the wall of the middle portion of the device body positioned to receive the lug to oppose the biasing force of the resilient member and to restrain the needle holder from moving away from the front end of the device body;

at least one retraction wing extending from the wall of the middle portion at a point adjacent to where the shoulder receives the lug; and, a tab coupled to the retraction wing positioned such that when the retraction wing is appropriately moved the tab pushes the lug off of the shoulder releasing the needle holder to respond to the bias of the resilient member.

7. The winged IV set of claim 6 wherein:

the arm extending from the needle holder is a pair of arms;

each of the pair of arms terminates in a lug;

the resilient member is a spring;

the shoulder in the wall of the middle portion of the device body is at least one shoulder positioned to receive each of the lugs to oppose the biasing force of the spring;

the retraction wing is a pair of retraction wings, each extending from the wall of the middle portion at a point adjacent to where the shoulder receives one of the lugs; wherein the retraction wings have a folded and an unfolded position; and, wherein each of the retraction wings has a tab coupled to the retraction wing and positioned such that when the retraction wing is folded the tab pushes one of the lugs off of the shoulder releasing the needle holder to respond to the bias of the spring.

8. A winged IV set comprising:

a device body having a front end, a back end, a middle portion comprising a longitudinally extended wall, and a hollow portion between the front and back ends and bounded by the wall of the middle portion;

a pair of approximately opposing handling wings extending from the wall of the middle portion of the device body;

a needle holder within the hollow portion of the device body;

a pair of approximately opposing arms extending from the needle holder;

each of the pair of approximately opposing arms terminating in a lug;

a needle extending outwardly from the needle holder in the direction of the front end of the device body;

a spring in contact with the device body and the needle holder and positioned to create a biasing force on the needle holder away from the front end of the device body;

a pair of approximately opposing shoulders in the wall of the middle portion of the device body, each positioned to receive one of the lugs to oppose the biasing force of the spring and to restrain the needle holder from moving away from the front end of the device body;

a pair of approximately opposing retraction wings, each extending from the wall of the middle portion at a point adjacent to where one of the pair of approximately opposing shoulders receives one of the lugs; and, each of the approximately opposing retraction wings having a tab coupled to the retraction wing and positioned such that when the retraction wing is folded towards the other of the retraction wings, the tab pushes one of the lugs off of one of the shoulders releasing the needle holder to respond to the bias of the spring.

9. The winged IV set of claim 8 further comprising:

a second pair of approximately opposing shoulders in the wall of the middle portion of the device body towards the back end of the device body, each positioned to receive one of the lugs to restrain the needle holder from moving toward the front end of the device body and to keep the needle completely within the hollow portion of the device body;

and wherein the spring is positioned and sized such that the biasing force on the needle holder will continue at least until the lugs move completely behind the second pair of approximately opposing shoulders.

10. The winged IV set of claim 9 wherein:

the needle holder further comprises a hollow nipple extending from an end of the needle holder opposite the needle.

11. The winged IV set of claim 10 wherein:

the needle holder contains a hollow passage linking the needle and the nipple in fluid communication.

12. The winged IV set of claim 8 wherein:

a plane approximately defined by the pair of approximately opposing handling wings parallels a plane approximately defined by the pair of approximately opposing retraction wings when in the unfolded position; and, the wall of the middle portion of the device body has a planar surface parallel to the planes defined by the handling wings and the retraction wings.

13. The winged IV set of claim 12 wherein:

the plane approximately defined by the pair of approximately opposing handling wings and the plane approximately defined by the pair of approximately opposing retraction wings when in the unfolded position are approximately congruent.

14. The winged IV set of claim 13 wherein:

the wall of the middle portion of the device body has a planar surface approximately congruent with the planes defined by the handling wings and the retraction wings.

15. The winged IV set of claim 9 wherein:

a plane approximately defined by the pair of approximately opposing handling wings parallels a plane approximately defined by the pair of approximately opposing retraction wings when in the unfolded position; and, the wall of the middle portion of the device body has a planar surface parallel to the planes defined by the handling wings and the retraction wings.

16. The winged IV set of claim 15 wherein:

the plane approximately defined by the pair of approximately opposing handling wings and the plane approximately defined by the pair of approximately opposing retraction wings when in the unfolded position are approximately congruent.

17. The winged IV set of claim 16 wherein:

the wall of the middle portion of the device body has a planar surface approximately congruent with the planes defined by the handling wings and the retraction wings.

* * * * *